United States Patent

McLoughlin et al.

[11] 4,049,808
[45] Sept. 20, 1977

[54] 2-PHENYL ETHYL MORPHOLINE COMPOUNDS

[75] Inventors: Bernard Joseph McLoughlin; Allen John Guildford, both of Macclesfield, England

[73] Assignee: Imperial Chemical Industries Limited, London, England

[21] Appl. No.: 735,124

[22] Filed: Oct. 22, 1976

Related U.S. Application Data

[62] Division of Ser. No. 567,011, April 10, 1975, Pat. No. 4,010,266.

[30] Foreign Application Priority Data

May 7, 1974 United Kingdom ............... 20013/74

[51] Int. Cl.² .................. C07D 265/30; A61K 31/535
[52] U.S. Cl. ............................ 424/248.4; 424/248.58; 544/106; 544/174
[58] Field of Search ...................... 260/247, 247.7 Z; 424/248.4, 248.58

[56] References Cited

U.S. PATENT DOCUMENTS 3,366,631  1/1968  Kalm ..................................... 260/247

OTHER PUBLICATIONS

McLoughlin et al., "Chem Abstracts", vol. 84 (1976), No. 44089z.

Primary Examiner—Henry R. Jiles
Assistant Examiner—R. W. Ramsuer
Attorney, Agent, or Firm—Cushman, Darby & Cushman

[57] ABSTRACT

Morpholine derivatives, typically those of the formula:

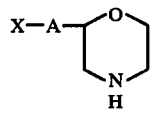

wherein A is an ethylene or vinylene radical and X is a phenyl radical optionally substituted by one or two substituents selected from halogen atoms, alkyl and alkoxy radicals of 1 to 6 carbon atoms and aryloxy radicals of 1 to 6 carbon atoms, the aryloxy radicals themselves being optionally substituted by one or two substituents selected from halogen atoms and alkyl radicals of 1 to 4 carbon atoms, and the pharmaceutically-acceptable acid-addition salts thereof. Processes for making these compounds, pharmaceutical compositions containing them and a method of restoring to normal abnormal mental states in warm-blooded animals are also disclosed.

8 Claims, No Drawings

2-PHENYL ETHYL MORPHOLINE COMPOUNDS

This is a division of application Ser. No. 567,011, filed Apr. 10, 1975, now U.S. Pat. No. 4,010,266.

This invention relates to morpholine derivatives which possess psychotropic properties.

According to the invention there is provided a morpholine derivative of the formula:

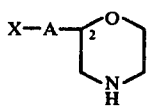
I wherein A stands for an ethylene (—CH$_2$CH$_2$—) or vinylene (—CH=CH—) radical and X stands for a phenyl radical which may optionally be substituted by one or two substituents selected from halogen atoms, alkyl and alkoxy radicals of 1 to 6 carbon atoms, and aryloxy radicals of 6 to 10 carbon atoms, the aryloxy radicals themselves being optionally substituted by one or two substituents selected from halogen atoms and alkyl radicals of 1 to 4 carbon atoms; and the pharmaceutically-acceptable acid-addition salts thereof.

It will be observed that the morpholine derivative of the invention contains an asymmetric carbon atom, that marked 2 in formula I. The racemic form of the compound of the formula I may therefore be resolved into 2 optically-active forms. It is to be understood that this invention encompasses the racemic form of the compound of the formula I and any optically-active enantiomeric form which possesses the useful properties of the compounds of the invention, as hereafter defined, it being a matter of common general knowledge how to resolve a racemate into its optically-active isomers and determine the biological properties thereof.

It is also to be understood that when A is a vinylene radical, it may be in the cis or trans form, and that the position of the optional substituent in the phenyl ring in X is defined according to the usual numbering system in which the carbon atom which is directly linked to A is numbered 1.

A particular value for the optional substituent in X is a fluorine, chlorine or bromine atom or a methyl, methoxy, ethoxy or phenoxy radical.

A particular value for A is an ethylene or trans vinylene radical.

Particular groups of compounds of the invention are as follows:

Those wherein X carries a single optional substituent:

Those wherein A stands for an ethylene or trans vinylene radical and X stands for a phenyl radical which is unsubstituted or which is substituted by a fluorine, chlorine or bromine atom or a methyl, methoxy or phenoxy radical in the 2- or 4-position:

Those wherein A stands for an ethylene radical and X stands for a phenyl radical which is unsubstituted or which is substituted by a phenoxy radical in the 2-position or in which A stands for a trans vinylene radical and X stands for a phenyl radical which is unsubstituted or which is substituted by a chlorine or bromine atom or methyl or phenoxy radical in the 2-position or by a methoxy radical in the 4-position or in which A stands for a cis vinylene radical and X stands for an unsubstituted phenyl radical:

Those wherein A stands for an ethylene radical and X stands for a phenyl radical which is substituted by a methyl radical in the 2-position or by a fluorine atom in the 4-position:

Particular compounds of the invention are described in the Examples and of those preferred compounds are those wherein A stands for an ethylene radical and X stands for a phenyl radical which is unsubstituted or which is substituted by a phenoxy radical in the 2-position or A stands for a trans vinylene radical and X stands for a phenyl radical which is unsubstituted or which is substituted by an ethoxy radical in the 2-position, and the salts thereof as defined above. These preferred compounds are active on the RHL test (see later) at does below 10 mg./kg.

A suitable pharmaceutically-acceptable acid-addition salt of the morpholine derivative of the invention is, for example, a hydrochloride, hydrobromide, phosphate or sulphate, or a citrate, acetate, maleate or oxalate.

The morpholine derivative of the invention may be manufactured by methods known in themselves for the manufacture of chemically analogous compounds, for example a process, in which X and A have the meanings stated above, characterised by:

a. replacing by hydrogen the radical R$^1$ in a compound of the formula:

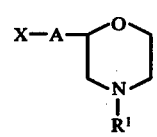
II in which R$^1$ is an alkanoyl or optionally substituted alkoxycarbonyl radical of up to 6 carbon atoms, an aroyl, α-arylalkyl or aryloxycarbonyl radical of up to 11 carbon atoms or a cyano radical;

b. for those compounds in which A is an ethylene radical, reduction of a compound of the formula:

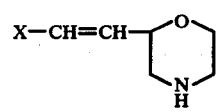
III with hydrogen in the presence of a catalyst;

c. for those compounds in which A is a vinylene radical, dehydration of a compound of the formula:

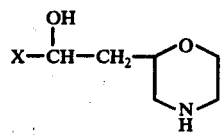
IV d. for those compounds in which A is an ethylene radical, reaction of a compound of the formula IV with hydrogen in the presence of a catalyst;

e. cyclisation of a compound of the formula:

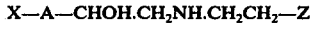

X—A—CHOH.CH$_2$NH.CH$_2$CH$_2$—Z   V wherein Z stands for a displaceable halogen atom or sulphonyloxy radical, in the presence of a base;

f. reduction of a compound of the formula:

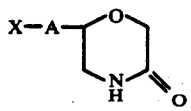

VI g. for those compounds in which A is an ethylene radical, desulphurisation of a compound of the formula:

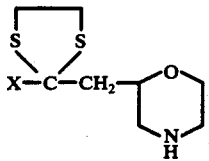

VII h. for those compounds in which A is a trans vinylene radical, isomerisation of a compound of the formula:

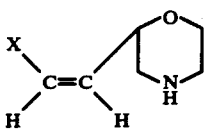

VIII i. for those compounds in which A is a vinylene radical, removal of the elements of hydrogen and halogen from a compound of the formula:

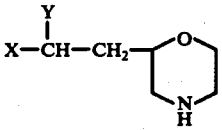

IX wherein Y is a halogen atom; or j. for a compound which is an optically-active enantiomer, resolution of the racemic compound of the formula I by conventional means, or by use of any of processes (a) to (i) in which the intermediate of the formula II, III, IV, V, VI, VII, VIII or IX is itself a resolved isomer.

In process (a) when $R^1$ is an alkanoyl, optionally substituted alkoxycarbonyl, aroyl or aryloxycarbonyl radical it may, for example, be an acetyl, ethoxycarbonyl, benzoyl or phenoxycarbonyl radical respectively and may be replaced by hydrogen by hydrolysis with an acid or a base, for example with hydrochloric or hydrobromic acid or sodium or potassium hydroxide, in a diluent or solvent such as acetic acid, ethanol or water or a mixture of any two or these. When $R^1$ is an optionally substituted alkoxycarbonyl radical, for example an alkoxycarbonyl radical of at least 3 carbon atoms which is substituted on the β carbon atom of the alkyl group by at least one chlorine or bromine atom, for example when $R^1$ is a 2,2,2-trichloroethoxycarbonyl radical, it may be replaced by hydrogen by reaction with zinc, for example by zinc in the presence of a dilute acid, for example acetic acid. When $R^1$ is a cyano radical, it may be replaced by hydrogen by reaction with a complex metal hydride, for example lithium aluminium hydride, in a diluent or solvent such as diethyl ether or tetrahydrofuran. All the above reactions may be accelerated or completed by the application of heat, for example by heating to the boiling point of the diluent or solvent.

When $R^1$ is an α-arylalkyl radical, for example the benzyl radical, it may be replaced by hydrogen by hydrogenolysis. The hydrogenolysis may be carried out by means of hydrogen in the presence of a palladium-on-charcoal catalyst, at ambient temperature and atmospheric pressure in a diluent or solvent such as ethanol, and may be accelerated by addition of an acidic catalyst, for example hydrochloric acid.

Processes (b) and (d) may be carried out by means of hydrogen in the presence of a palladium-on-charcoal catalyst at ambient temperature and atmospheric pressure in a diluent or solvent such as ethanol.

Process (c) may be carried out, for example, by means of toluene-p-sulphonic acid in a solvent such as toluene or xylene, the water formed during the reaction being removed azeotropically, or with methyltriphenoxy phosphonium iodide in hexamethylphosphoric triamide as solvent.

In process (e) Z may be, for example, a chlorine or bromine atom or a radical of the formula $OSO_2R^2$ in which $R^2$ stands for a hydroxy radical or for a lower alkyl or an aryl radical, for example the methyl, ethyl, phenyl or p-tolyl radical. The base used in the reaction may be an alkali or alkaline earth metal hydroxide, for example sodium, potassium or barium hydroxide. The reaction may be carried out in a diluent or solvent, for example water, an alcohol, for example methanol or ethanol or an ether, for example diethyl ether, dimethoxyethane or tetrahydrofuran and it may be carried out at ambient temperature or at a temperature up to the boiling point of the diluent or solvent, for example a temperature of between 40° and 100° C.

Process (f) may be carried out with a complex metal hydride, for example lithium aluminium hydride, in a diluent or solvent such as diethyl ether or tetrahydrofuran, and the reaction may be accelerated or completed by the application of heat, for example by heating up to the boiling point of the diluent or solvent.

Process (g) may be carried out, for example, in the presence of a catalyst such as Raney nickel, in a diluent or solvent such as toluene or xylene.

Process (h) may be carried out, for example, with a thiophenol such as thiophenol or 4-chlorothiophenol in the presence of a catalyst such as azobisisobutyronitrile and in a duluent or solvent such as toluene or xylene, or with an acid such as hydrochloric acid in a solvent such as water, and may be accelerated or completed by the application of heat, for example heating to the boiling point of the diluent or solvent.

Process (i) may be carried out by heating with a base, for example 1,5-diazabicyclo[5.4.0]undec-5-ene, in a diluent or solvent such as dimethylsulphoxide.

Where the structures of the starting material and the product permit, two of the above processes may be performed simultaneously. Thus, using hydrogenation conditions, processes (a) and (b) or (a) and (d) may be carried out together.

The starting material for use in processes (a), (b) and (h) in which A is a vinylene radical may be prepared, as described in Example 1, by reaction of 4-benzyl-2-(toluene-p-sulphonyloxymethyl)morpholine and lithium iodide to give 4-benzyl-2-iodomethylmorpholine. This compound is then reacted with triphenyl phosphine to give 4-benzylmorpholin-2-ylmethyl triphenyl phosphonium iodide which is subsequently reacted with a base to form the corresponding phosphorane. This intermediate is reacted in situ with the appropriate substituted benzaldehyde to give 4-benzyl-2-(β-substituted phenylvinyl)-morpholine as a mixture of cis and trans isomers. These isomers are, if necessary, separated by chromatography, or by fractional crystallisation of an acid-addition salt, and if required this N-benzyl derivative is used to form other N-substituted starting materials. Thus reaction with an aryl or optionally substituted alkyl chloroformate gives the corresponding phenoxy- or alkoxy-carbonyl derivative, or reaction with cyanogen bromide gives the corresponding N-cyano derivative.

The starting material for use in processes (c) and (d) may be prepared, as described in Example 17 and 18, by reaction of 4-benzyl-2-(toluene-p-sulphonyloxymethyl)-morpholine with sodium cyanide followed by reaction of the resulting 4-benzyl-2-cyanomethylmorpholine with an aryl lithium or aryl Grignard. The resulting ketone is then reduced to the corresponding alcohol which is obtained as a mixture of diastereoisomers.

The starting material for use in process (e) in which A is an ethylene radical may be prepared, as described in Example 13, by reaction of an appropriately substituted phenylpropionaldehyde with a mixture of trimethyloxosulphonium iodide and sodium hydride. The resulting epoxide is then reacted with 2-aminoethyl hydrogen sulphate. Alternatively, the starting material for use in process (e) in which A is a vinylene radical may be prepared, for example, by reaction of 1-bromo-4-phenylbut-3-en-2-one with 2-aminoethyl hydrogen sulphate followed by reduction of the ketonic group to the corresponding alcohol.

The starting material for use in process (f) may be prepared, as described in Example 14, by reaction of 1,2-epoxy-4-phenylbutane with benzylamine followed by reaction of the product with chloracetylchloride. The N-benzyl-N-chloroacetyl derivative thus obtained is cyclised to the N-benzylmorpholone with sodium methoxide and the benzyl group subsequently replaced by hydrogen by reaction with sodium in liquid ammonia.

The starting material for use in process (g) may be obtained, as described in Example 19, by reaction of the appropriate 4-benzyl-2-phenacylmorpholine with cyanogen bromide to give the corresponding 4-cyano derivative which is then reacted with ethane dithiol. The cyano group in the resulting dithioketal is then replaced by hydrogen by reduction with lithium aluminium hydride.

The starting material for use in process (i) may be prepared, for example, by direct halogenation of the corresponding derivative in which A is an ethylene radical.

The compounds of the invention are psychotropic agents, that is they have the ability to restore to normal an abnormal mental state in warm-blooded animals. For example the compounds of the invention display antidepressant and sedative activity. By antidepressant activity we mean that clinical effect produced by the tricyclic antidepressants such as imipramine when used to treat the clinical syndrome known as depression.

Antidepressant activity is demonstrated by reversal of reserpine-induced hypothermia in mice, a standard test (Askew, *Life Sciences,* 1963, 2, 725) used in the art to determine the relative quantitative antidepressant activities in a series of chemically-related compounds.

Sedative activity is demonstrated by reduction of the spontaneous activity in mice as measured by photobeam interruption, a standard test (Riley and Spinks, *J. Pharm. Pharmacol.,* 1958, 10, 662-663) used in the art for assessing sedative activity and compounds active on this test are therefore useful as sedatives, for example for exerting a calming effect on excitable or aggressive animals.

All the compounds exemplified in this specification are active on at least one of the above tests though not all the compounds are active on both tests. In addition analgesic activity is widespread throughout the series.

The reversal of reserpine-induced hypothermia, known as the RHL test, is carried out as follows:

Mice are kept in a constant temperature room maintained at $21 \pm 1°$ C. Each member of groups of 4 mice is given reserpine (2 mg. of base per kg. bodyweight, given subcutaneously as the acetate). Seventeen hours later the oesophageal temperature ($T_0$) of each mouse is recorded by means of an orally-inserted probe coupled to an electric thermometer which is calibrated in degrees Centigrade and which can be read to $0.1°$ C. Immediately after the temperature measurement the mice are dosed orally with the test compound, or with imipramine, each mouse in a group of 4 being given the same substance, and the oesophageal temperatures are again recorded after 4 hours ($T_4$). The compound under test is dosed at serial dilutions, e.g. 100, 30, 10, 3, 1, 0.3, 0.1 mg./kg. Imipramine is used as the control. Over a large number of tests it has been found that 3 mg./kg. of imipramine produces an average rise in the temperature of a reserpinised mouse of $3°$ C. At 1 mg./kg. it produces an average rise of $1.7°$ C. A test compound which at a certain does level gives a rise in temperature equal to or greater than that given by 1 mg./kg. of imipramine, dosed to a different set of mice on the same day, is adjudged "active" at that dose.

The measurement of the reduction of the spontaneous activity in mice, is carried out as follows:

Groups of 6 mice are dosed orally with the compound under test and 45 minutes later are placed individually in cages provided with a central horizontal scanning photobeam. The number of beam interruptions in the first 45 minutes is recorded and the percentage inhibition of movement relative to control animals is calculated. The compound is considered active if the amount of movement of the dosed animals is reduced by more than a third compared to control animals.

All the compounds exemplified in this specification are active on at least one of these two tests at a dose of less than or equal to 100 mg./kg. of the free base while at the same dose showing no obvious signs of toxicity.

The compound 2-[β-(2-phenoxyphenyl)ethyl morpholine has an oral $LD_{50}$ in mice of 1000 mg./kg. and the compound 2-[β-(2-methylphenyl)ethyl]morpholine has an oral $LD_{50}$ in mice of 550 mg./kg.

According to a further feature of the invention there is provided a pharmaceutical composition which comprises as active ingredient a morpholine derivative of the invention in association with a pharmaceutically-acceptable diluent or carrier.

The pharmaceutical composition may be, for example, in a form suitable for oral or parenteral administration, for which purposes it may be formulated by means known to the art into the form of, for example, tablets, capsules, aqueous or oily solutions or suspensions, emulsions, sterile injectable aqueous or oily solutions or suspensions, or dispersible powders.

The pharmaceutical composition of the invention may also contain, in addition to the morpholine derivative or salt thereof, one or more known drugs selected from neuroleptic-sedative agents, for example chlorpromazine, prochlorperazine, trifluoperazine and haloperidol; other sedative drugs and tranquillizers, for example chlordiazepoxide, phenobarbitone and amylobarbitone; β-adrenergic blocking agents, for example propranolol; drugs used in the treatment of Parkinson's disease, for example benzhexol; and other antidepressant drugs, for example imipramine, desipramine, amitriptyline, and nortriptyline; drugs of the amphetamine type; and monoamineoxidase inhibitors, for example phenelzine and mebanazine.

A preferred pharmaceutical composition of the invention is one suitable for oral administration in unit dosage form, for example tablets and capsules, which contain between 20 and 200 mg. of active ingredient, or one suitable for intravenous or intramuscular injection, for example a sterile aqueous solution containing between 0.5 and 4% w/w of active ingredient.

The pharmaceutical composition of the invention will normally be administered to man for the purpose of restoring to normal an abnormal mental state at such a dose that each patient receives a total oral dose of between 50 mg. and 1 g. of active ingredient per day, of a total intravenous or intramuscular dose of between 10 and 200 mg. per day, the composition being administered 2 or 3 times per day.

The invention is illustrated, but not limited, by the following Examples:

EXAMPLE 1

A solution of sodium methylsulphinylmethide is prepared in the usual way from an 80% mineral oil dispersion of sodium hydride (4.36 g.) and dimethyl sulphoxide (350 ml.). Water (2.1 ml.) is added and the mixture is stirred and heated at 60° C. while a solution of 4-phenoxycarbonyl-2-[β-(4-methoxyphenyl)-cis-vinyl]-morpholine (6.1 g.) in dimethyl sulphoxide (20 ml.) is added. The mixture is stirred and heated at 50°-60° C. for 3 hours. The mixture is cooled, diluted with water (500 ml.) and saturated brine (500 ml.), and extracted with ethyl acetate (3 × 300 ml.). The combined extracts are washed with water (3 × 200 ml.), dried over anhydrous magnesium sulphate and the solvent is removed from the filtered solution by evaporation under reduced pressure. The residue is converted into its maleate salt which is crystallised from a mixture of ethyl acetate and methanol to give 2-[β-(4-methoxyphenyl)-cis-vinyl]-morpholine hydrogen maleate, m.p. 158°-159° C.

The 4-phenoxycarbonyl-2-[β-(4-methoxyphenyl)-cis-vinyl]morpholine used as starting material may be obtained as follows:

A mixture of 4-benzyl-2-(toluene-p-sulphonyloxymethyl)morpholine (120 g.), lithium iodide monohydrate (100 g.), and dry dimethylformamide (800 ml.) is stirred and heated at 100°-110° C. in an atmosphere of nitrogen for 2 hours. The mixture is cooled, diluted with water (1.5 l.), and extracted with petroleum ether (b.p. 60°-80° C.) (3 × 500 ml.). The combined extracts are dried and the solvent is removed. There is thus obtained 4-benzyl-2-iodomethylmorpholine, m.p. 42°-45° C., which is not further purified.

A solution of 4-benzyl-2-iodomethylmorpholine (100.4 g.) and triphenyl phosphine (82.5 g.) in dry xylene (1 l.) is stirred and refluxed for 24 hours. The mixture is cooled and filtered and the solid is recrystallised from methanol. There is thus obtained 4-benzylmorpholin-2-ylmethyl triphenyl phosphonium iodide, m.p. 271°-272° C.

A mixture of 4-methoxybenzaldehyde (4.08 g.) and 4-benzylmorpholin-2-ylmethyl triphenyl phosphonium iodide (17.37 g.) in dry dimethylformamide (500 ml.) is stirred at ambient temperature in an atmosphere of nitrogen. An 80% mineral oil dispersion of sodium hydride (0.9 g.) is added and the mixture is stirred and the temperature is slowly raised to 110° C. during 1 hours. The mixture is stirred at 110° C. for 12 hours, then it is cooled, diluted with water (500 ml.) and extracted with ethyl acetate (3 × 500 ml.). The ethyl acetate extracts are combined and washed with water (3 × 500 ml.) and dried over anhydrous magnesium sulphate, and the solvent is removed in the usual way. There is thus obtained a gum which consists of a mixture of the cis and trans ethylene derivatives and triphenyl phosphine oxide. This mixture dissolved in toluene (30 ml.) is chromatographed on magnesium silicate (500 g.). Elution with toluene (2 l.) gives 4-benzyl-2-[β-(4-methoxyphenyl)-cis-vinyl]morpholine which gives a hydrogen oxalate hemihydrate, m.p. 120°-122° C. after crystallisation from a mixture of methanol and ethyl acetate. Further elution with toluene (1 l.) gives 4-benzyl-2-[β-(4-methoxyphenyl)-trans-vinyl]morpholine which gives a hydrogen oxalate, m.p. 191°-192° C., from ethyl acetate and methanol.

To a solution of 4-benzyl-2-[β-(4-methoxyphenyl)cis-vinyl]morpholine (6.0 g.) in dry methylene chloride (150 ml.) is added phenyl chloroformate (2.74 ml.). The mixture is stirred at ambient temperature for 4 hours. The solution is washed with 2N hydrochloric acid solution (50 ml.), water (50 ml.), saturated sodium bicarbonate solution (50 ml.) and dried, and the solvent removed by evaporation. There is thus obtained 4-phenoxycarbonyl-2-[β-(4-methoxyphenyl)-cis-vinyl]morpholine as an oil which is not purified further.

EXAMPLE 2

A solution of 4-cyano-2-[β-(4-methoxyphenyl)-trans-vinyl]morpholine in tetrahydrofuran (10 ml.) is added dropwise to a stirred suspension of lithium aluminium hydride (0.25 g.) in dry ether (60 ml.). The mixture is stirred at ambient temperature for 3 hours. The mixture is cooled in an ice bath and there are successively added water (0.25 ml.), 2N sodium hydroxide solution (0.25 ml.) and water (0.75 ml.). The mixture is stirred for 15 minutes, filtered, and the filtrate is evaporated under reduced pressure. The residue is converted to the maleate salt which is crystallised from a mixture of methanol and ethyl acetate to give 2-[β-(4-methoxyphenyl)-trans-vinyl]morpholine maleate, m.p. 153°-154° C.

The 4-cyano-2-[β-(4-methoxyphenyl)-trans-vinyl]-morpholine used as starting material may be prepared as follows:

To a solution of 4-benzyl-2-[β-(4-methoxyphenyl)-trans-vinyl]morpholine (1.03 g.) in dry methylene chloride (100 ml.) is added cyanogen bromide (0.39 g.). The mixture is stirred at ambient temperature for 12 hours, then the solvent is removed under reduced pressure. The residue is dissolved in ethyl acetate (100 ml.) and the organic solution is washed successively with 2N hydrochloric acid solution (50 ml.), water (50 ml.) and saturated sodium chloride solution (50 ml.) and dried over anhydrous magnesium sulphate. Removal of the solvent gives 4-cyano-2-[β-(4-methoxyphenyl)-trans-vinyl]morpholine.

EXAMPLE 3

The process described in Example 1 is repeated using the appropriately substituted 4-phenoxycarbonyl derivative as starting material in place of 4-phenoxycarbonyl-2-[β-(4-methoxyphenyl)-cis-vinyl]morpholine and the following compounds are thus obtained:

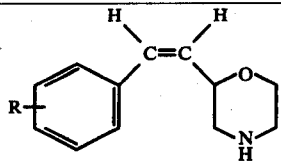

| R | Salt | m.p. (° C.) | Recrystallisation solvent |
|---|---|---|---|
| 3-MeO | oxalate hemihydrate | 157–159 | methanol/ethyl acetate |
| H | oxalate | 163–164 | methanol/ethyl acetate |
| 2-Cl | hydrogen maleate | 112–114 | methanol/ethyl acetate |
| 2-PhO | hydrogen maleate | 148–149 | methanol/ethyl acetate/ether |
| 2-Me | hydrogen maleate | 139–140 | methanol/ethyl acetate |

The starting materials for the above compounds may be prepared by repeating the process described in the fourth part of Example 1 using the appropriate aldehyde as starting material in place of 4-methoxybenzaldehyde. The following compounds are thus obtained:

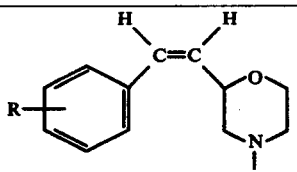

| R | Salt | m.p.(° C.) | Recrystallisation solvent |
|---|---|---|---|
| 3-MeO | hydrogen oxalate hemihydrate | 183–185 | methanol/ether |
| H | hydrogen oxalate hemihydrate | 153–154 | methanol/ethyl acetate |
| 2-Cl | hydrogen oxalate | 131–132 | methanol/ethyl acetate |
| 2-PhO | hydrogen oxalate | 154–155 | methanol/ethyl acetate |
| 2-Me | hydrogen oxalate | 186–187 | methanol/methyl acetate |

These 4-benzyl derivatives are then reacted with phenyl chloroformate as described in the fifth part of Example 1. The 4-phenoxycarbonyl derivatives thus obtained are used without purification.

EXAMPLE 4

A solution of 4-benzyl-2-[β-(2-ethoxyphenyl)-cis-vinyl]morpholine hydrogen oxalate (1.4 g.) in ethanol (50 ml.) is hydrogenated at ambient temperature and pressure over a 30% palladium on charcoal catalyst (0.3 g.) until no more hydrogen is absorbed. The mixture is filtered and the filtrate is evaporated under reduced pressure. The residue is crystallised from a mixture of methanol and ether to give 2-[β-(2-ethoxyphenyl)ethyl]morpholine hydrogen oxalate, m.p. 119°–121° C.

The 4-benzyl-2-[β-(2-ethoxyphenyl)-cis-vinyl]-morpholine hydrogen oxalate used as starting material may be obtained by repeating the process described in the fourth part of Example 1 using 2-ethoxybenzaldehyde in place of 4-methoxybenzaldehyde as starting material. The product has m.p. 156°–158° C. on recrystallisation from ethanol/ether.

EXAMPLE 5

The process described in Example 4 is repeated using the appropriate 4-benzyl derivatives as starting materials. The following compounds are thus obtained as their hydrogen oxalates:

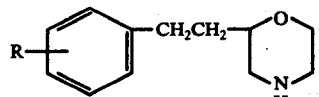

| R | m.p.(° C.) | Recrystallisation solvent |
|---|---|---|
| 3-MeO | 164–165 | methanol/ether |
| H | 151–152 | methanol/ethyl acetate |

EXAMPLE 6

A solution of 2-[β-(4-methoxyphenyl)-cis-vinyl]morpholine (1.4 g.) in ethanol (40 ml.) and saturated ethanolic hydrochloric acid (0.5 ml.) is hydrogenated at ambient temperature and pressure over a 5% palladium on charcoal catalyst (0.5 g.) until no more hydrogen is absorbed. The mixture is filtered and the filtrate is evaporated under reduced pressure. The residual oil is basified with 2N sodium hydroxide solution and the product is obtained in the conventional manner by extraction with ethyl acetate. The free base is converted to its maleate salt and recrystallised from a mixture of methanol and ethyl acetate. There is thus obtained 2-[β-(4-methoxyphenyl)ethyl]morpholine hydrogen maleate, m.p. 152°–153° C.

EXAMPLE 7

The process described in Example 6 is repeated using the appropriate 2-cis-vinylmorpholine as starting material, and the following compounds are thus prepared after recrystallisation from methanol/ethyl acetate:

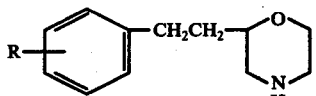

| R | Salt | m.p.(° C.) |
|---|---|---|
| 4-Cl | hydrogen maleate | 145–146 |
| 2-Cl | hydrogen oxalate | 148–149 |
| 2-PhO | hydrogen maleate | 158–159 |
| 2-Me | hydrogen maleate | 135–136 |

The 2-[β-(4-chlorophenyl)-cis-vinyl]morpholine hydrogen maleate used as starting material may be obtained by repeating the process described in the fourth part of Example 1 using 4-chlorobenzaldehyde as starting material in place of 4-methoxybenzaldehyde. There is thus obtained 4-benzyl-2-[β-(4-chlorophenyl)-cis-vinyl]morpholine hydrogen oxalate, m.p. 181°–182° C. on recrystallisation from methanol/ethyl acetate.

This product is reacted with phenyl chloroformate according to the process described in the fifth part of Example 1 and the product, which is not purified, is subjected to the process described in the first part of Example 1 to give 2-[β-(4-chlorophenyl)-cis-vinyl]morpholine hydrogen maleate, m.p. 129°-130° C. on recrystallisation from methanol/ethyl acetate/ether.

EXAMPLE 8

The process described in Example 1 is repeated using 4-phenoxycarbonyl-2-[β-(2-chlorophenyl)-trans-vinyl]-morpholine as starting material and there is thus obtained 2-[β-(2-chlorophenyl)-trans-vinyl]morpholine hydrogen maleate, m.p. 145°-146° C. on recrystallisation from methanol/ethyl acetate.

The 4-phenoxycarbonyl-2-[β-(2-chlorophenyl)-trans-vinyl]morpholine used as starting material may be prepared by repeating the process described in the fourth part of Example 1 using 2-chlorobenzaldehyde as starting material. There is thus obtained 4-benzyl-2-[β-(2-chlorophenyl)-trans-vinyl]morpholine hydrogen oxalate, m.p. 175°-176° C. on recrystallisation from methanol/ethyl acetate. The corresponding 4-phenoxycarbonyl derivative is then obtained by repeating the process described in the fifth part of Example 1 and is used without further purification.

EXAMPLE 9

The process described in Example 2 is repeated using the appropriately substituted 4-cyano derivative as starting material in place of 4-cyano-2-[β-(4-methoxyphenyl)-trans-vinyl]morpholine and the following compounds are thus obtained after recrystallisation from methanol/ethyl acetate:

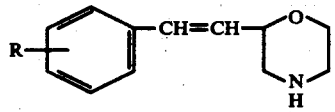

| Double Bond Configuration | R | Salt | m.p.(° C.) |
|---|---|---|---|
| Trans | H | hydrogen maleate hemihydrate | 121-122 |
| Trans | 2-OEt | hydrogen maleate | 134-135* |
| Trans | 3-OMe | hydrogen maleate | 138-141 |
| Trans | 4-Cl | hydrogen maleate | 146-147 |
| Trans | 4-F | hydrogen maleate | 145-146 |
| Trans | 2-OPh | sesquioxalate | 140-142 |
| Trans | 2-Me | hydrogen maleate | 139-141 |
| Trans | 3-Cl | hydrogen maleate | 133-134 |
| Trans | 2-Br | hydrogen maleate | 144-146 |
| Cis | 2-Br | hydrogen maleate | 130-131 |
| Cis | 4-F | hydrogen maleate | 142-143 |

*Recrystallised from ethyl acetate/petroleum ether (b.p. 60-80° C.)

The starting materials for the above compounds may be prepared
a. by repeating the process described in the fourth part of Example 1 using the appropriate aldehyde as starting material in place of 4-methoxybenzaldehyde. The following compounds are thus obtained as their hydrogen oxalates after recrystallisation from methanol/ethyl acetate:

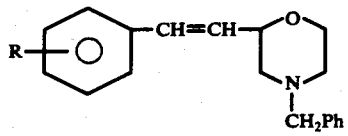

| Double Bond Configuration | R | m.p.(° C.) |
|---|---|---|
| Cis | 4-F | 180-181 (decomp.) |
| Trans | 4-F | 177-178 (decomp.) |
| Trans | H | 171-173 (decomp.) |
| Cis | 2-Br | Not characterised |
| Trans | 2-Br | Not characterised |
| Trans | 3-Cl | Not characterised | or b. by a process exemplified as follows:

A solution of 4-benzyl-2-(β-phenyl-cis-vinyl)-morpholine (0.84 g.) thiophenol (0.89 g.) and azobisisobutyronitrile (0.01 g.) in dry toluene (10 ml.) is heated at 70° C. for 8 hours. The mixture is cooled and diluted with ether (50 ml.) and the organic solution is extracted with 5% w/v aqueous sodium hydroxide solution (3 × 20 ml.). The organic solution is dried and the solvent is removed under reduced pressure and there is thus obtained an oil which consists of 4-benzyl-2-(β-phenyl-trans-vinyl)morpholine contaminated with a small amount of the cis isomer. The trans compound is purified by conversion to its oxalate salt by conventional means and crystallisation from methanol/ethyl acetate. There is thus obtained 4-benzyl-2-(β-phenyl-trans-vinyl)morpholine hydrogen oxalate, m.p. 171°-173° C. (decomp.) By using the appropriate substituted cis compound in place of 4-benzyl-2-(β-phenyl-cis-vinyl)morpholine and repeating the process described immediately above, the following compounds are obtained:

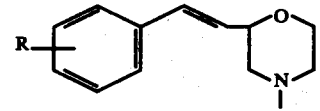

| R | Salt | m.p.(° C.) | Recrystallisation solvent |
|---|---|---|---|
| 2-OEt | hydrogen oxalate hemihydrate | 182-184 (decomp.) | methanol/ethyl acetate |
| 3-OMe | hydrochloride | 191-192 | methanol/ethyl acetate |
| 4-Cl | hydrogen oxalate | 190-191 | methanol/ether | or (c) by a process exemplified as follows:

A solution of 4-benzyl-2-(β-phenyl-cis-vinyl)-morpholine (0.75 g.) in dry dimethylformamide (50 ml.) is stirred and a 30% w/w mineral oil dispersion of sodium hydride (0.82 g.) is added. The mixture is slowly heated to 110° C. in an atmosphere of nitrogen and the temperature is maintained at 110° C. for 2 hours. The mixture is cooled and diluted with water and the product is obtained by extraction with ethyl acetate. There is thus obtained an oil which consists of 4-benzyl/2-μβ-phenyl-trans-vinyl]morpholine contaminated with a small amount of 4-benzyl-2-(β-phenylethylidene)morpholine. This oil is dissolved in toluene (5 ml.) and chromatographed on magnesium silicate (50 g.). Elution with toluene (200 ml.) gives the 4-benzyl-2-[β-phenylethylidene]morpholine which is discarded. Further elution with toluene containing 5% v/v ethyl acetate gives the 4-benzyl-2-[β-phenyl-trans-vinyl]morpholine which is used without further purification.

By using the appropriate substituted cis compound in place of 4-benzyl-2-[β-phenyl-cis-vinyl]morpholine, in the process described immediately above, there are obtained 4-benzyl-2-[β-(2-methylphenyl)-trans-vinyl]- morpholine and 4-benzyl-2-[β-(2-phenoxyphenyl)-trans-vinyl]morpholine which are used without further purification.

These 4-benzyl derivatives are then reacted with cyanogen bromide as described in the second part of Example 2. The 4-cyano derivatives thus obtained are used without purification.

EXAMPLE 10

The process described in Example 2 is repeated using 4-cyano-2-(β-phenylethyl)morpholine as starting material in place of 4-cyano-2-[β-(4-methoxyphenyl)-trans-vinyl]morpholine and there is thus obtained 2-(β-phenylethyl)morpholine, as its hydrogen oxalate salt, m.p. 151°–152° C. after crystallisation from methanol/ethyl acetate.

The 4-cyano-2-(β-phenylethyl)morpholine used as starting material may be obtained as follows:

A solution of 4-benzyl-2-(β-phenyl-cis-vinyl)-morpholine hydrogen oxalate hemihydrate (0.5 g.) in absolute ethanol (50 ml.) is hydrogenated at ambient temperature and pressure over a platinum catalyst obtained by pre-hydrogenation of platinum oxide (0.1 g.) until one equivalent (32 ml.) of hydrogen is absorbed. The mixture is filtered and the solvent is removed from the filtrate. The residue is crystallised from methanol/ethyl acetate and there is thus obtained 4-benzyl-2-(β-phenylethyl)morpholine hydrogen oxalate, m.p. 168°–169° C.

This compound is then reacted with cyanogen bromide using the process described in the second part of Example 2. There is thus obtained 4-cyano-2-(β-phenylethyl)morpholine which is used without further purification.

EXAMPLE 11

To a solution of 4-(2,2,2-trichloroethoxycarbonyl)-2-[β-(2-phenoxyphenyl)-cis-vinyl]morpholine (0.34 g.) in acetic acid (20 ml.) is added zinc dust (0.4 g.). The mixture is stirred at ambient temperature for 12 hours then basified with 2N sodium hydroxide solution and the product is extracted with ethyl acetate (3 × 50 ml.). The ethyl acetate is removed from the dried combined extracts by evaporation and the residue is converted to its maleate salt and recrystallised from methanol/ethyl acetate to give 2-[β-(2-phenoxyphenyl)-cis-vinyl]morpholine hydrogen maleate, m.p. 148°–149° C.

The 4-(2,2,2-trichloroethoxycarbonyl)-2-[β-(2-phenoxyphenyl)-cis-vinyl]morpholine used as starting material may be obtained by repeating the process described in the last part of Example 1, using equivalent amounts of 4-benzyl-2-[β-(2-phenoxyphenyl)-cis-vinyl]-morpholine and 2,2,2-trichloroethoxycarbonyl chloride in place of 4-methoxyphenyl)-cis-vinyl]morpholine and phenyl chloroformate respectively. The product is obtained as an oil which is not purified further.

EXAMPLE 12

The process described in Example 6 is repeated using an equivalent amount of 2-[β-(4-fluorophenyl)-cis-vinyl]-morpholine or 2-[β-(4-fluorophenyl)-trans-vinyl]morpholine as starting material in place of 2-[β-(4-methoxyphenyl)-cis-vinyl]-morpholine and there is thus obtained 2-[β-(4-fluorophenyl)-ethyl]morpholine hydrogen maleate, m.p. 141°–142° C. on recrystallisation from methanol/ethyl acetate.

EXAMPLE 13

A mixture of 1,2-epoxy-4-phenylbutane (1.48g.) and 2-aminoethyl hydrogen sulphate (7.05 g.) in methanol (7.5 ml.) and sodium hydroxide solution (18N, 2.8 ml.) is stirred at ambient temperature for 2 hours. The 2-(2-hydroxy-4-phenylbutyl)aminoethyl hydrogen sulphate formed as intermediate is not isolated is cyclised in situ as follows:

A further portion of sodium hydroxide solution (18N, 5.6 ml. ) is added and the mixture is stirred and heated at 60° C. for 24 hours. Water (100 ml.) is added and the mixture is extracted with ethyl acetate (3 × 50 ml.). The combined ethyl acetate extracts are themselves extracted with hydrochloric acid solution (2N, 3 × 50 ml.) and the organic solution is discarded. The acidic extracts are combined and basified with 18N sodium hydroxide solution. The basic solution is extracted with ethyl acetate (3 × 50 ml. ) and the combined organic extracts are dried and the solvent is removed under reduced pressure. The residue is converted to its oxalate salt which is crystallised from methanol/ethyl acetate to give 2-(β-phenylethyl)morpholine hydrogen oxalate, m.p. 151°–152° C.

The 1,2-epoxy-4-phenylbutane used as starting material may be obtained as follows:

A solution of trimethyloxosulphonium iodide (2.64 g.) in dry dimethylsulphoxide (50 ml. ) is stirred at 50°–60° C. in an atmosphere of nitrogen and an 80% w/w mineral oil dispersion of sodium hydride (0.36 g.) is added. Stirring and heating are continued until the solution is clear and no more hydrogen is evolved. A solution of 3-phenylpropionaldehyde (1.34 g.) in dry dimethyl sulphoxide (10 ml.) is added and the mixture is stirred at 50°–60° C. in an atmosphere of nitrogen for 3 hours. The mixture is cooled and diluted with water (200 ml.), and the product is obtained by extraction with ethyl acetate (3 × 80 ml.). Removal of the solvent from the combined extracts gives 1,2-epoxy-4-phenylbutane as an oil which is not further purified.

EXAMPLE 14

A solution of 2-(β-phenylethyl)morpholine-5-one (430 mg.) in dry tetrahydrofuran (4 ml.) is added to a stirred suspension of lithium aluminium hydride (200 mg.) in dry ether (20 ml.) at such a rate that the mixture refluxes gently. After complete addition, the mixture is stirred and refluxed for 2 hours, then it is cooled and there are successively added water (0.2 ml.), sodium hydroxide solution (2N, 0.2 ml.) and water (0.6 ml.) and stirring is continued for 15 minutes. The mixture is filtered and the filtrate is evaporated under reduced pressure to give 2-(β-phenylethyl)morpholine as an oil which may be converted to its hydrogen oxalate salt, m.p. 151°–152° C. or its hydrogen maleate salt, m.p. 120°–122° C. on recrystallisation from methanol/ethyl acetate.

The 2-(β-phenylethyl)morpholin-5-one used as starting material may be obtained as follows:

A mixture of 1,2-epoxy-4-phenylbutane (5.91 g.) and benzylamine (10 ml.) is stirred and heated at 140° C. for 18 hours. Excess benzylamine is removed by distillation under reduced pressure (20 mm.) (bath temperature 110° C.). The residual oil is converted to its hydrogen oxalate salt which is crystallised from methanol/ethyl acetate, to give 1-benzylamino-4-phenylbutan-2-olhydrogen oxalate, m.p. 196° C.

This product is converted back to the free base by conventional means and the free base (3.7 g.) is dissolved in dry methylene chloride (37 ml.) and triethylamine (2 ml.) is added. The mixture is stirred and cooled to 0° C. and a solution of chloroacetyl chloride (1.64 g.) in dry methylene chloride (10 ml.) is added dropwise during 15 minutes. The mixture is stirred at ambient temperature for 2 hours then it is washed with hydrochloric acid solution (2N, 2 × 20 ml.) and water (20 ml.) and dried and the solvent is removed under reduced pressure. There is thus obtained 1-N-chloroacetylbenzylamino-4-phenylbutan-2-ol which is not further purified.

This product is dissolved in methanol (50 ml.) and a solution of sodium methoxide prepared from sodium metal (0.33 g.) and methanol (10 ml.) is added. The mixture is stirred and refluxed for 18 hours. The mixture is cooled and filtered and the filtrate is evaporated under reduced pressure. The residue is dissolved in ethyl acetate (50 ml.) and the solution is washed successively with water (20 ml.) hydrochloric acid solution (2N, 20 ml.), water (20 ml.) and saturated brine (20 ml.). The ethyl acetate solution is dried and the solvent removed under reduced pressure to give 4-benzyl-2-($\beta$-phenylethyl)morpholin-5-one which is not further purified.

A solution of this compound (2.2 g.) is dry tetrahydrofuran (10 ml.) is added dropwise during 10 minutes to a stirred solution of sodium (0.332 g.) in liquid ammonia (50 ml.). After complete addition, sodium (0.1 g.) is added and the mixture is stirred for 20 minutes. Ammonium chloride (1 g.) is added and the ammonia is allowed to evaporate. The residue is partitioned between water (50 ml.) and ethyl acetate (50 ml.) and the ethyl acetate layer is separated and dried and the solvent is removed under reduced pressure. The residue is crystallised from diethyl ether to give 2-($\beta$-phenylethyl)morpholin-5-one, m.p. 100°-102° C.

EXAMPLE 15

A solution of 2-($\beta$-phenyl-cis-vinyl)morpholine (0.189 g.), thiophenol (0.1 g.) and azobisisobutyronitrile (0.03 g.) in dry toluene (30 ml.) is stirred and heated at 110° C. for 18 hours. The mixture is cooled and diluted with ether (50 ml.) and the organic solution is washed successively with sodium hydroxide solution (2N, 3 × 20 ml.) and water (20 ml.) and dried and the organic solvent is removed under reduced pressure. There is thus obtained 2-($\beta$-phenyl-trans-vinyl)morpholine which is converted to its hydrogen maleate salt, m.p. 123°-124° C. after crystallisation from methanol/ethyl acetate.

The same product may be obtained from the same starting material by repeating the above process using 4-chlorothiophenol (0.35 g.) in place of thiophenol and heating for 2 hours.

EXAMPLE 16

A solution of 2-[$\beta$-(4-methoxyphenyl)-cis-vinyl]-morpholine (0.219 g.), thiophenol (0.3g.) and azobisisobutyronitrile (0.03g.) in dry toluene (3 ml.) is stirred and heated at 70°-80° C. for 12 hours. The product is obtained as described in Example 15 and there is thus obtained 2-[$\beta$-(4-methoxyphenyl)trans-vinyl]morpholine hydrogen maleate, m.p. 153°-154° C. on recrystallisation from methanol/ethyl acetate.

EXAMPLE 17

A solution of 4-benzyl-2-phenacylmorpholine hydrochloride (0.95 g.) in ethanol (18 ml.) and perchloric acid (1 drop) is hydrogenated at ambient temperature and pressure over a 30% w/w palladium-on-charcoal catalyst (0.1 g.) until no more hydrogen is absorbed. The mixture is heated to reflux, filtered through diatomaceous earth and the filtrate is evaporated under reduced pressure. The residue is dissolved in water, basified with 2N sodium hydroxide solution and extracted with ether (3 × 10 ml.). The combined ether extracts are washed with brine, dried over magnesium sulphate and then evaporated in vacuo. The free base is converted to its oxalate salt and recrystallised from a mixture of methanol and ethyl acetate to give 2-[$\beta$-phenylethyl]morpholine hydrogen oxalate, m.p. 151-153° C.

The 4-benzyl-2-phenacylmorpholine used as starting material may be obtained as follows:

A mixture of finely ground sodium cyanide (39.6 g.) and 4-benzyl-2-(toluene-p-sulphonyloxymethyl)morpholine (144.4 g.) in dimethyl sulphoxide (600 ml.) is stirred and heated at 60°-65° C. for 3.5 hours. The mixture is cooled, diluted with water (6 l.) and extracted with ether (3 × 2 l.). The ether extracts are combined and washed with brine (2 × 1 l.) and dried over anhydrous magnesium sulphate and the solvent removed by evaporation in vacuo. The residue is recrystallised from petroleum ether (b.p. 40°-60° C.) to give 4-benzyl-2-cyanomethylmorpholine, m.p. 62° C.

A phenyl lithium solution is prepared by dropwise addition of a solution of dry bromobenzene (26.25 ml.) in sodium dried ether (125 ml.) to a mechanically stirred mixture of small pieces of lithium (3.5 g.) in sodium dried ether (125 ml.) in an atmosphere of argon and at such a rate as to maintain gentle reflux. After complete addition of the bromobenzene solution, a further portion of dry bromobenzene (5 ml.) is added and the stirred mixture is heated under reflux for 30 minutes. The reaction mixture is cooled to −20° C. (acetone/solid $CO_2$) and a solution of 4-benzyl-2-cyanomethylmorpholine (27.0 g.) in sodium-dried ether (135 ml.) is added dropwise with stirring and at such a rate as to maintain the temperature at −20° C. to −15° C. The mixture is stirred at −15° C. for 15 minutes, added with stirring to ice cold hydrochloric acid solution (N, 2 l.) and stirred for 15 minutes during which time a solid crystallises from solution. The product is filtered, washed with a small volume of water, followed by ether and is then dried in vacuo. Recrystallisation from isopropanol gives 4-benzyl-2-phenacylmorpholine hydrochloride, m.p. 184°-186° C.

EXAMPLE 18

A mixture of 2-($\beta$-hydroxy-$\beta$-phenylethyl)morpholine (3.1 g.) and methyltriphenoxy phosphonium iodide (38 g.) in hexamethylphosphoric triamide (120 ml.) is stirred and heated at 75° C. in an atmosphere of nitrogen for 1 hour. The cooled mixture is diluted with water (1200 ml.), basified with 18N sodium hydroxide solution and extracted with ethyl acetate (3 × 250 ml.). The combined ethyl acetate extracts are washed with 50% v/v aqueous brine (2 × 200 ml.), dried over anhydrous sodium sulphate and evaporated in vacuo. The residual yellow oil is dissolved in ether and added to ethereal oxalic acid (one molar equivalent) giving a sticky solid. The ether is decanted off and fresh ether is added and decanted and the residue is triturated with hot acetone. There is thus obtained 2-($\beta$-phenyl-trans-vinyl)morpholine hydrogen oxalate, m.p. 173°-176° C. on recrystallisation from methanol. The hydrogen oxalate can be converted to the free base and thereafter to the hydrogen maleate, m.p. 122°–123° C. on recrystallisation from ethanol/ethyl acetate.

The 2-(β-hydroxy-β-phenylethyl)morpholine used as starting material may be obtained as follows:

A solution of 4-benzyl-2-phenacylmorpholine (9.2 g.) in absolute ethanol (200 ml.) is hydrogenated at ambient temperature and pressure over a 5% w/w palladium-on-charcoal catalyst (1.0 g.). After 3 days, further 5% w/w palladium-on-charcoal catalyst (0.3 g.) is added and hydrogenated for a further 24 hours. The mixture is heated to reflux, filtered through diatomaceous earth and the filtrate is evaporated in vacuo. There is thus obtained 2-(β-hydroxy-β-phenylethyl)-morpholine which is used without further purification.

EXAMPLE 19

A mixture of 2-(2-phenyl-[1,3]-dithiol-2-ylmethyl)-morpholine (0.5g. ) and Raney nickel (4.0 g.) in dry toluene (50 ml.) is stirred at 15–20° C. for 30 minutes. The mixture is filtered through diatomaceous earth and the residue is washed thoroughly with toluene. The toluene solution is evaporated in vacuo and the residual gum is dissolved in ether and added to excess ethereal oxalic acid solution. There is thus obtained 2-(β-phenylethyl)morpholine hydrogen oxalate, m.p. 151°–153° C. on recrystallisation from methanol/ethyl acetate.

The 2-(2-phenyl-[1,3]-dithiol-2-ylmethyl)morpholine used as starting material may be obtained as follows:

A solution of 4-benzyl-2-phenacylmorpholine (18.6 g.) and cyanogen bromide (8.2 g.) in methylene chloride (186 ml.) is stirred at ambient temperature overnight. The reaction solution is diluted with methylene chloride (700 ml.) and is washed with aqueous HCl (2N, 125 ml.) and water (2 × 125 ml.), and dried over anhydrous magnesium sulphate and the solvent removed in vacuo. The residue is dissolved in the minimum of toluene and subjected to chromatography on magnesium silicate (700 g.), eluting consecutively with toluene, 25% v/v chloroform/toluene, 50% chloroform/toluene, chloroform and 50% v/v ethyl acetate/chloroform. The toluene fractions are discarded and the remainder are combined and evaporated in vacuo. There is thus obtained 4-cyano-2-phenacylmorpholine, m.p. 76°–77° C. on recrystallisation from isopropanol.

A mechanically stirred mixture of 4-cyano-2-phenacylmorpholine (12.2 g.), ethane dithiol (5.3 ml.) and sodium dried benzene (36 ml.) is saturated with dry hydrogen chloride gas and stirred at ambient temperature for 6 hours. The reaction mixture is diluted with water (50 ml.), basified with 2N sodium hydroxide solution and diluted with petroleum ether (b.p. 60°–80° C., 350 ml.). The cooled suspension is filtered, the residual solid is washed with water and there is thus obtained 4-cyano-2-(2-phenyl-[1,3]-dithiol-2-ylmethyl)-morpholine, m.p. 110°–111° C. on recrystallisation from absolute ethanol.

A solution of 4-cyano-2-(2-phenyl-[1,3]-dithiol-2-ylmethyl)morpholine (9.0 g.) in dry tetrahydrofuran (180 ml.) is added dropwise to stirred suspension of lithium aluminium hydride (1.14 g.) in dry tetrahydrofuran (90 ml.) in an atmosphere of nitrogen and with cooling at 0°–5° C. The mixture is stirred at 0°–5° C. for 1.5 hours and then treated successively with water (1.14 ml.), sodium hydroxide solution (2N, 1.14 ml.) and water (3.42 ml.). The mixture is stirred at 0°–5° C. for 15 minutes and then filtered through diatomaceous earth and the residue is washed well with tetrahydrofuran. The tetrahydrofuran solution is evaporated in vacuo and the residue is heated with HCl solution (2N, 45 ml.) on a stream bath for 30 minutes. The cooled solution is diluted with water (45 ml.) and basified with ammonium hydroxide solution (s.g. 0.88) and extracted with ether (3 × 100 ml.). The combined ether extracts are washed with water, dried over anhydrous magnesium sulphate and filtered and the filtrate added to ethereal oxalic acid solution. The salt thus obtained is purified by recrystallisation from dimethylformamide/methanol and converted to its free base by suspending in chloroform, basifying with ammonium hydroxide solution (s.g. 0.88) and washing with water. The aqueous layer is extracted with chloroform (2 × 50 ml.), the combined chloroform extracts are washed with water (2 × 50 ml.) and dried over anhydrous potassium carbonate and the solvent removed in vacuo. There is thus obtained 2-(2-phenyl-[1,3]-dithiol-2-ylmethyl)-morpholine, m.p. 86°–88° C. on recrystallisation from toluene/petroleum ether (b.p. 60°–80° C.)

EXAMPLE 20

A mixture of 2-(β-hydroxy-β-phenylethyl)morpholine (2.3 g. ) and toluene-p-sulphonic acid (2.4 g.) in sodium-dried toluene (50 ml.) is heated at reflux for 2 hours with stirring in an atmosphere of nitrogen under a Dean and Stark water separator. The mixture on cooling gives 2-(β-phenyl-transvinyl)morpholine toluene-p-sulphonate, m.p. 170.5°–172.5° C. on recrystallisation from absolute ethanol. The toluene-p-sulphonate can be converted to the free base and thereafter to the hydrogen maleate, m.p. 122°–124° C. on recrystallisation from ethanol/ethyl acetate.

EXAMPLE 21

A solution of 2-(β-phenyl-cis-vinyl)morpholine hydrogen maleate (0.2 g.) in hydrochloric acid (11N, 10 ml.) is heated at 90°–100° C. for 30 minutes. The mixture is cooled, diluted with water (50 ml.), rendered basic by addition of ammonia solution and extracted with ethyl acetate (3 × 30 ml.). The ethyl acetate extracts are combined and dried over anhydrous magnesium sulphate and the solvent is removed under reduced pressure. There is thus obtained 2-(β-phenyl-trans-vinyl)-morpholine, characterised as the hydrogen maleate, m.p. 123°–124° C. on recrystallisation from methanol-/ethyl acetate.

EXAMPLE 22

A solution of 2-(β-hydroxy-β-phenylethyl)morpholine hydrochloride (1 g.) in ethanol (30 ml.) and 60% w/v aqueous perchloric acid solution (2 drops) is hydrogenated at ambient temperature and pressure over a 30% w/w palladium-on-charcoal catalyst (0.1 g.) until no more hydrogen is absorbed. The mixture is filtered through diatomaceous earth and the filtrate is evaporated in vacuo. The residue is dissolved in water (20 ml.), basified with aqueous sodium hydroxide solution (2N) and extracted with ether (3 × 20 ml.). The combined ether extracts are washed with brine (1 × 25 ml.), dried over anhydrous magnesium sulphate, concentrated in vacuo and added to an ethereal solution of oxalic acid to give 2-(β-phenylethyl)-morpholine hydrogen oxalate, m.p. 151°–152° C. on recrystallisation from methanol/ethyl acetate.

What we claim is:

1. A morpholine derivative of the formula:

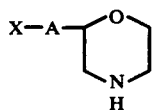

wherein A stands for an ethylene (—CH₂CH₂—) radical and X stands for a phenyl radical, unsubstituted or substituted by one or two substituents selected from the group consisting of halogen atoms, alkyl and alkoxy radicals of 1 to 6 carbon atoms and phenoxy, unsubstituted or substituted by one or two substituents selected from halogen atoms and alkyl radicals of 1 to 4 carbon atoms; and the pharmaceutically-acceptable acid-addition salts thereof.

2. A morpholine derivative as claimed in claim 1 in which the optional substituents in X are selected from fluorine, chlorine and bromine atoms, and methyl, methoxy, ethoxy and phenoxy radicals.

3. A morpholine derivative as claimed in claim 1 in which X carries a single optional substituent.

4. A morpholine derivative as claimed in claim 1 in which A stands for an ethylene radical and X stands for a phenyl radical which is unsubstituted or which is substituted by a fluorine, chlorine, or bromine atom or a methyl, methoxy or phenoxy radical in the 2- or 4- position.

5. A morpholine derivative as claimed in claim 1 in which A stands for an ethylene radical and X stands for a phenyl radical which is unsubsituted or which is substituted by a phenoxy radical in the 2- position.

6. A morpholine derivative as claimed in claim 1 in which A stands for an ethylene radical and X stands for a phenyl radical which is substituted by a methyl radical in the 2- position or by a fluorine atom in the 4- position.

7. A sedative composition comprising an effective amount of a morpholine derivative as claimed in claim 1 in association with a pharmaceutically-acceptable diluent or carrier.

8. A method of restoring to normal an abnormal mental state in a warm-blooded animal by sedation which comprises administering thereto an effective amount of a compound of claim 1.